(12) United States Patent
Bar-Cohen et al.

(10) Patent No.: US 11,724,104 B2
(45) Date of Patent: Aug. 15, 2023

(54) EPICARDIAL LEAD DESIGN

(71) Applicants: Children's Hospital Los Angeles, Los Angeles, CA (US); University of Southern California, Los Angeles, CA (US)

(72) Inventors: Yaniv Bar-Cohen, South Pasadena, CA (US); Gerald Loeb, South Pasadena, CA (US); Li Zhou, Los Angeles, CA (US); Raymond Peck, Los Angeles, CA (US); Steven Nutt, Irvine, CA (US)

(73) Assignees: CHILDREN'S HOSPITAL LOS ANGELES, Los Angeles, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 17/336,003

(22) Filed: Jun. 1, 2021

(65) Prior Publication Data

US 2022/0054826 A1 Feb. 24, 2022

Related U.S. Application Data

(63) Continuation of application No. 14/889,853, filed as application No. PCT/US2014/037366 on May 8, 2014, now Pat. No. 11,020,588.
(Continued)

(51) Int. Cl.
*A61N 1/05* (2006.01)
*A61N 1/375* (2006.01)
(Continued)

(52) U.S. Cl.
CPC ........... *A61N 1/0587* (2013.01); *A61N 1/059* (2013.01); *A61N 1/362* (2013.01); *A61N 1/3756* (2013.01);
(Continued)

(58) Field of Classification Search
CPC .. A61N 1/0587; A61N 1/37512; A61N 1/059; A61N 1/362; A61N 1/37205; A61N 1/37288; A61N 1/3756; A61N 1/3787
See application file for complete search history.

(56) References Cited

U.S. PATENT DOCUMENTS 7,634,313 B1 * 12/2009 Kroll .................. A61N 1/37288
607/2
7,848,823 B2 * 12/2010 Drasler ................ A61N 1/0573
607/32

FOREIGN PATENT DOCUMENTS

WO WO-9315791 A1 * 8/1993 ........... A61N 1/0592

* cited by examiner

*Primary Examiner* — Tammie K Marlen
(74) *Attorney, Agent, or Firm* — Moazzam & Associates, LLC (57) ABSTRACT

The present invention provides an advancement in the art of cardiac pacemakers. The invention provides a novel and unobvious pacemaker system that comprises at least one pacemaker and that is, to a large extent, self-controlled, allows for long-term implantation in a patient, and minimizes current inconveniences and problems associated with battery life. The invention further includes a mechanism in which at least two pacemakers are implanted in a patient, and in which the pacemakers communicate with each other at the time of a given pacing or respiratory event, without any required external input, and adjust pacing parameters to respond to the patient's need for blood flow. The invention further provides a novel design for a pacemaker in which the pacemaker electrode is connected to the pacemaker body by a lead that is configured to allow the pacemaker to lie parallel to the epicardial surface and to reduce stress on the pacemaker and heart tissue.

11 Claims, 8 Drawing Sheets

Related U.S. Application Data (60) Provisional application No. 61/924,253, filed on Jan. 7, 2014, provisional application No. 61/820,809, filed on May 8, 2013.

(51) Int. Cl.
 *A61N 1/362* (2006.01)
 *A61N 1/372* (2006.01)
 *A61N 1/378* (2006.01)

(52) U.S. Cl.
 CPC ....... *A61N 1/3787* (2013.01); *A61N 1/37205* (2013.01); *A61N 1/37288* (2013.01); *A61N 1/37512* (2017.08)

EPICARDIAL LEAD DESIGN

CROSS-REFERENCE TO RELATED APPLICATIONS

This application is a continuation of U.S. patent application Ser. No. 14/889,853, filed Nov. 8, 2015, now U.S. Pat. No. 11,020,588; which is a national stage application of PCT/US2014/037366, filed May 8, 2014; which claims priority to U.S. Provisional Patent Application Ser. No. 61/924,253, filed on Jan. 7, 2014, and to U.S. Provisional Patent Application Ser. No. 61/820,809, filed on May 8, 2013, the contents of which are hereby incorporated by reference herein in their entirety into this disclosure.

BACKGROUND OF THE INVENTION

Field of the Invention

The present invention relates to the field of medical devices. More specifically, the present invention relates to a new design for an epicardial lead, which allows a pacemaker to lie parallel to the myocardium and pericardial sac with little or no stress on the pacemaker electrode or myocardial tissue.

Description of Related Art

Since their introduction in the 1950s, cardiac pacemakers have generally taken the form of a surgically implanted pulse generator powered by a primary cell and connected to one or more flexible leads that pass through the major veins into the right atrium and/or right ventricle, where they are anchored to the myocardium by a corkscrew-shaped electrode. Less common variants introduced over the years and relevant to this invention include epicardially placed electrodes and leads and inductively rechargeable secondary cells for power.

It is generally desirable to eliminate the need for open surgical implantation of any medical device and to eliminate the need for repeat implantation procedures when the primary power source is depleted. Any open surgery entails risks from anesthesia and wound-healing and generally results in substantial pain, discomfort, and limited motor function for days to weeks after surgery. Making the implant small enough to enable minimally invasive implantation techniques necessarily compromises the amount of energy that can be stored in the implant and its ability to detect and manage complex arrhythmias and multiple or intermittent conduction blocks among the various cardiac chambers.

The field of cardiac rhythm management has many mature products covered by patents describing various potential and implemented features and improvements. Within the past few years, major manufacturers have begun to talk about their development plans for "leadless pacemakers", which are intended to be surgically implanted on the epicardial surface of the left ventricle or intravenously attached to the endocardial wall of the right ventricle as a single, freestanding module. However, publicly available details regarding those pacemakers are not well known to the skilled artisan.

The present inventors and their colleagues have previously disclosed percutaneously implantable pacemakers for a fetus with a corkscrew electrode and a rechargeable battery, for example in U.S. patent application publication number 2012/0078267 (corresponding to WO 2010/141929). In addition, an insertion tool for neuromuscular stimulators using friction to affix an implant into the distal end of an insertion sleeve was described in Kaplan, H. M. and Loeb, G. E., "Design and fabrication of an injection tool for neuromuscular microstimulators." Annals of Biomedical Engineering, 37(9):1858-1870, 2009, and Loeb, G. E. and Richmond, F. J. R., "System for implanting a microstimulator", U.S. Pat. No. 6,214,032, issued Apr. 10, 2001. Further, generation of stimulation pulses during injection of a neuromuscular module to determine the correct location before release was described in Loeb, Gerald E., "Identification of target site for implantation of a microstimulator", U.S. Pat. No. 7,555,347, issued Jun. 30, 2009.

Other work in the field includes work directed toward detecting a current pulse emitted by one modular implant using another modular implant. An example of this technology was described for determining the distance between two neuromuscular implants in Sachs, N. A. and Loeb, G. E., "Development of a BIONic muscle spindle for prosthetic proprioception", *IEEE Trans. Biomedical Engineering*, 54(6):1031-1041, June 2007. In addition, an RF communication link for multiple modular neuromuscular implants was described in Rodriguez, N., Weissberg, J., Loeb, G. E., "Flexible Communication and Control Protocol for Injectable Neuromuscular Interfaces", *IEEE Transactions on Biomedical Circuits and Systems*, 1(1):19-27, March, 2007, and Loeb, G. E., Weissberg, J., Rodriguez, N., "Flexible communication and control protocol for a wireless sensor and microstimulator network", U.S. Pat. No. 7,593,776, issued Sep. 22, 2009. One method for generating a high-strength RF magnetic field and modulating its amplitude to transmit data is described in Troyk, P. R., Heetderks, W., Schwan, M. and Loeb, G. E., "Suspended carrier modulation of high-Q transmitters", U.S. Pat. No. 5,697,076, issued Dec. 9, 1997. The design of an injectable module incorporating a rechargeable lithium cell as part of the case and return electrode has been described in various patents and articles by Joseph Schulman et al. at the Alfred Mann Foundation in Valencia, Calif. And, inductively rechargeable cardiac pacemakers were sold briefly around the 1980s before the advent of lithium primary cells.

Injectable neuromuscular stimulators and their use for various medical indications are described in the following documents: Loeb, G. E. and Richmond, F. J. R., "Implantable microstimulator system for producing repeatable patterns of electrical stimulation", U.S. Pat. No. 6,175,764, issued Jan. 16, 2001; Loeb, G. E. and Richmond, F. J. R., "Implantable microstimulator system for prevention of disorders", U.S. Pat. No. 6,181,965, issued Jan. 30, 2001; Loeb, G. E. and Richmond, F. J. R., "Implantable microstimulator and systems employing the same", U.S. Pat. No. 6,051,017, issued Apr. 18, 2000; Loeb, G. E. and Schulman, J. H., "Implantable multichannel stimulator", U.S. Pat. No. 5,571,148, issued Nov. 5, 1996; Schulman, J. H., Loeb, G. E., Gord, J. C. and Strojnik, P., "Structure and method of manufacture of an implantable microstimulator", U.S. Pat. No. 5,405,367, issued Apr. 11, 1995; Loeb, G. E., "Implantable device having an electrolytic storage electrode", U.S. Pat. No. 5,312,439, issued May 17, 1994; Schulman, J. H., Loeb, G. E., Gord, J. C. and Strojnik, P., "Implantable microstimulator", U.S. Pat. No. 5,324,316, issued Jun. 28, 1994; Schulman, J. H., Loeb, G. E., Gord, J. C. and Stroynik, P., "Implantable microstimulator", U.S. Pat. No. 5,193,539, issued Mar. 18, 1993; and Schulman, J. H., Loeb, G. E., Gord, J. C. and Stroynik, P., "Structure and method of manufacture of an implantable microstimulator", U.S. Pat. No. 5,193,540, issued Mar. 18, 1993.

SUMMARY OF THE INVENTION

The present invention addresses needs in the art by providing an epicardial pacing system that comprises or consists of one or more implanted modules, implantation means for percutaneous implantation and fixation of the implanted modules, lead designs that permit a pacemaker to lie flat against (i.e., substantially parallel to) the epicardial surface, thus reducing strain on the pacemaker and heart tissue and allowing for unimpeded cardiac motion. As depicted in the Figures, a pacemaker according to the invention has i) a length or height and ii) a width or diameter, such as in the shape of a cylinder. As such, when referring to the pacemaker lying flat against or parallel to the epicardial surface, it is meant that the surface defining the length or height lies substantially flat or parallel to the epicardial surface while the surface defining the diameter or width is substantially perpendicular to the epicardial surface. In preferred embodiments, the pacing system further comprises extracorporeal equipment for programming, monitoring, and recharging the implanted modules. Through practice of the invention, one may achieve cardiac pacing via one or more implanted devices, each of which has a form factor that permits minimally invasive, percutaneous implantation and fixation. One may also achieve cardiac pacing without placing devices in direct contact with blood flow in the endovascular or endocardial spaces. The present invention also provides a full range of programmable demand and rate responsive pacing algorithms comparable to conventional cardiac pacemakers. Through practice of the invention, one can augment failed or inadequate pacing through additional minimally invasive implants without the requirement of removing previously implanted devices. The invention additionally enables unlimited functional lifetime of implanted devices by supporting wireless inductive recharging of secondary cells powering those devices via an extracorporeally generated electromagnetic field, and enables unlimited functional lifetime of implanted devices by encasing the electronic circuitry and its power supply in a hermetically and preferably watertight sealed package. Yet further, the invention can be implemented to minimize the deleterious effects of continuous myocardial motion on the connection between electrodes and electronic circuitry. This is achieved by incorporating a flexible, durable hinge that connects the electrode to the electronic circuitry.

In some embodiments, the present invention provides devices and systems for cardiac rhythm management for a broad range of medical conditions and situations in which conventional pacemaker technology is contra-indicated or difficult to implement, such as: patients with an infected pacemaker, lead or subacute bacterial endocarditis must usually have their pacemaker system entirely removed until after the infection has been eradicated by antibiotic therapy; certain blood clotting disorders might predispose the patient to thromboembolism from endovascular pacemaker leads; young patients (under 3 to 5 years of age) are generally not considered candidates for endocardial lead placement due to their small size; patients in generally poor health or with specific conditions that would affect wound healing or response to anesthesia should avoid surgery; certain conduction deficits require direct pacing of the left ventricle, which can be difficult or impossible to achieve via the conventional coronary sinus approach; patients who have experienced dislodgement or failure of an existing endovascular lead, which can interfere with the ability to install another such endovascular lead; young patients might need to undergo repeated replacement of their pacemaker battery over the course of their life, which increases risk of wound-healing complications such as infection, dehiscence, erosion, and extrusion; pacing of the right ventricle in an unpredictable subset of pacemaker patients results in heart failure due to asynchrony and can be treated by left ventricular pacing. It is to be understood that the present invention is not limited to the above listed conditions, but rather is intended to provide a desirable alternative to conventional cardiac pacemakers in most patients and conditions, as will be understood by physicians and others normally skilled in the art of cardiac rhythm management. It is also to be understood that the present invention can be augmented by other modules not described herein that may not be feasible to construct in minimally invasive form using currently available technologies, such as a percutaneously implanted defibrillator module. In addition, the present invention can augment other devices, such as a separately implanted defibrillator device, whereby the present invention allows a means of sensing cardiac activity and transmitting corresponding current pulses that are received by the other device in order to monitor cardiac activity. Such improvements and enhancements to the modular epicardial pacing system taught herein fall within the scope of this invention.

The present invention provides a novel micropacemaker design, and in particular a pacemaker lead design, to address the critical problem of complete heart block in patients of all sizes, including fetal patients, pediatric patients, and adult patients. Until recently, fetal heart block had no effective treatment except for early delivery because early attempts to implant an extra-uterine pacemaker with electrodes on the fetal heart invariably failed due to lead dislodgement from fetal movement. To address this problem, the present inventors designed a self-contained, single-chamber, rechargeable micropacemaker that can be completely implanted in the fetus without exteriorized leads, allowing for subsequent fetal movement without risk of electrode dislodgement. The present invention advances that concept to provide a percutaneous implantation scheme for micropacemakers and larger epicardial devices that provide demand pacing, variable rates, and a multi-chamber system via a modular configuration, as well as a battery having a life of potentially greater than six months between charges and being capable of being recharged wirelessly, which permits potentially decades of device life. The present invention further advances that concept by providing a lead design that reduces strain on the pacemaker electrode and on the myocardial tissue at the point of insertion of the pacemaker.

The device and system of the invention provides any one of, or any combination of two or more of, the following features: a percutaneous implantation technique to insert a single atrial or ventricular, or both an atrial and ventricular, pacemaker (e.g., micropacemaker, also referred to herein as a "modular device" or "implanted module") device via a pericardial approach to the epicardium (this is similar to current implantation techniques used to perform epicardial ablations); wireless communication between one or multiple modular devices, in which each device can correctly identify the actions of the other device(s) and/or report relevant data to a detection device external to the patient, without the power consumption and interference risks inherent in RF communication; and the ability to incorporate rate responsive pacing to adjust pacing rates automatically based on the patient's dynamic physiologic need. Conventional rate responsive pacemakers use accelerometers or thoracic impedance sensing that are not directly suitable for the modular devices of the present invention, so the present invention uses a method based on sensing respiratory rate from impulses emitted by one module and sensed by the other(s), or an external sensing device; and long-term pacing required by adult and pediatric populations is accommodated by incorporating custom versions of existing ceramic packaging and battery technologies.

BRIEF DESCRIPTION OF THE DRAWINGS

The accompanying drawings, which are incorporated in and constitute a part of this specification, illustrate embodiments of the invention, and together with the written description, serve to explain certain principles of the invention. The drawings and their accompanying textual description are not to be construed as limiting the scope of the invention in any way.

FIG. 6 illustrates various non-limiting mechanical configurations of the pacemaker body and electrode. FIGS. 6A and C depict physical relationships prior to implantation of the pacemaker, in which hinged lead 46 is constrained by mechanical pressure to allow base 43 (also referred to herein at times as a "barb"), and the pacemaker within waterproof case 42 to remain within insertion sheath 41 until the pacemaker is deployed. FIGS. 6B and D depict the relationship after implantation.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention, as broadly disclosed herein. Rather, the following discussion is provided to give the reader a more detailed understanding of certain aspects and features of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention.

Unless defined otherwise, all technical and scientific terms used herein have the same meaning as commonly understood by one of ordinary skill in the art to which the term belongs. Although any methods and materials similar or equivalent to those described herein can be used in the practice of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a pulse" includes a plurality of such pulses and reference to "the electrode" includes reference to one or more electrodes and equivalents thereof known to those skilled in the art. Furthermore, the use of terms that can be described using equivalent terms include the use of those equivalent terms. Thus, for example, the use of the term "patient" is to be understood to include the terms "human", "subject", and other terms used in the art to indicate one who is subject to a medical treatment.

Figure 1:
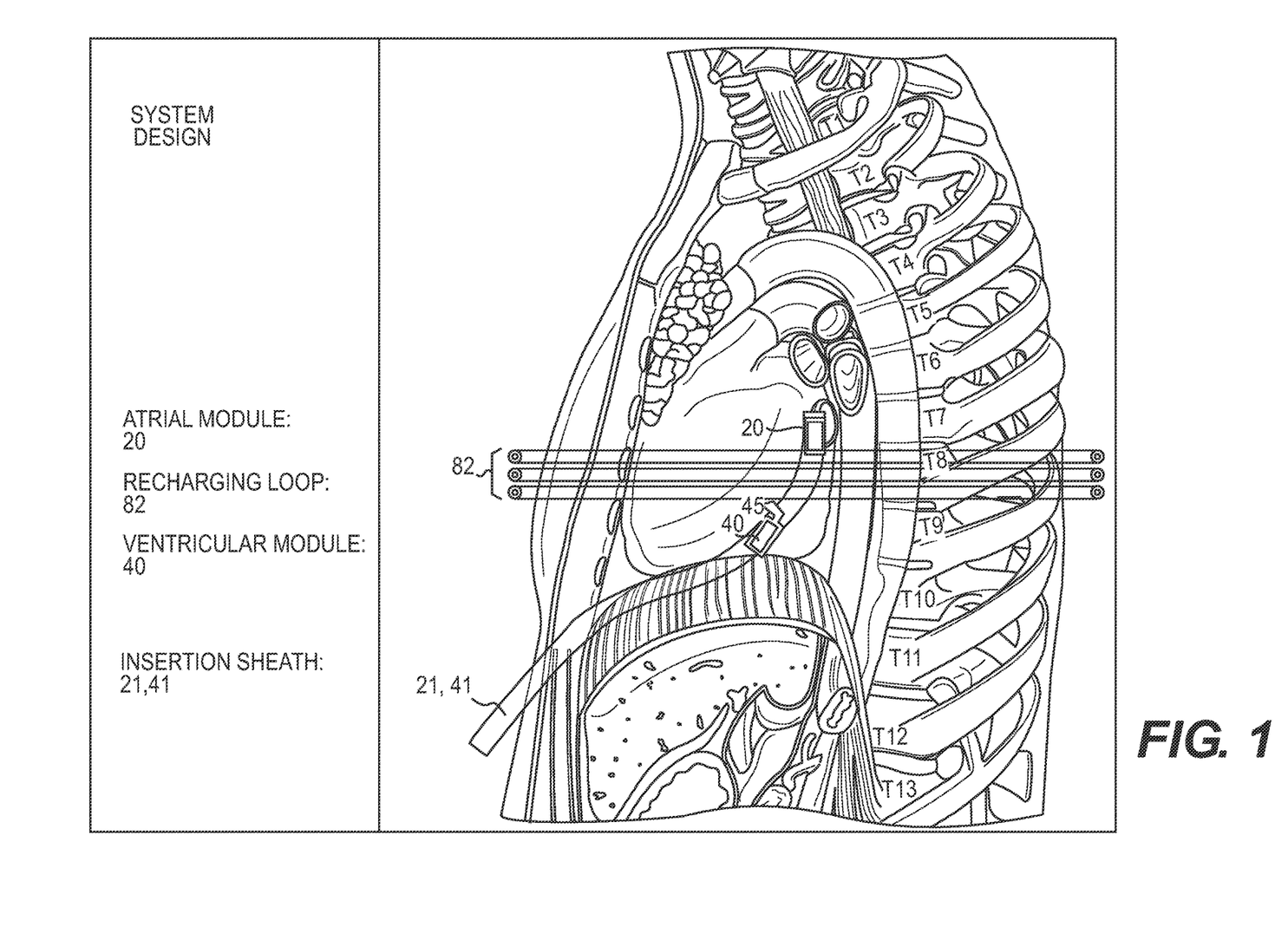
FIG. 1 shows an embodiment of the invention using two implanted modules in a preferred anatomical location and the route by which they are delivered there by the implantation means FIG. 2 provides a schematic block diagram of the electronic subsystems and wireless communication connections for both the implanted modules and extracorporeal equipment for embodiments where two implanted modules are used.
Figure 2:
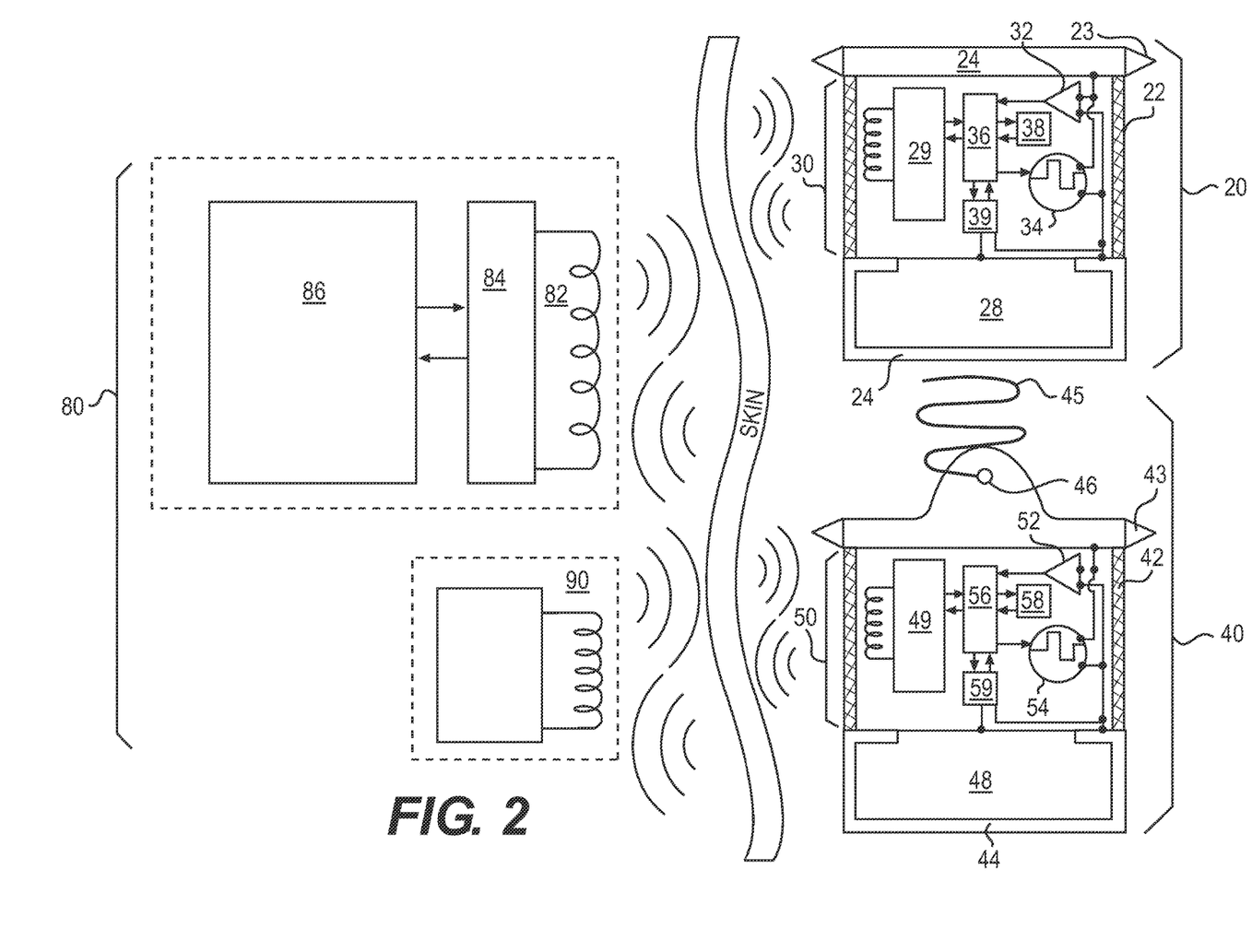
Figures 4A, 4B, 4C, 4D:
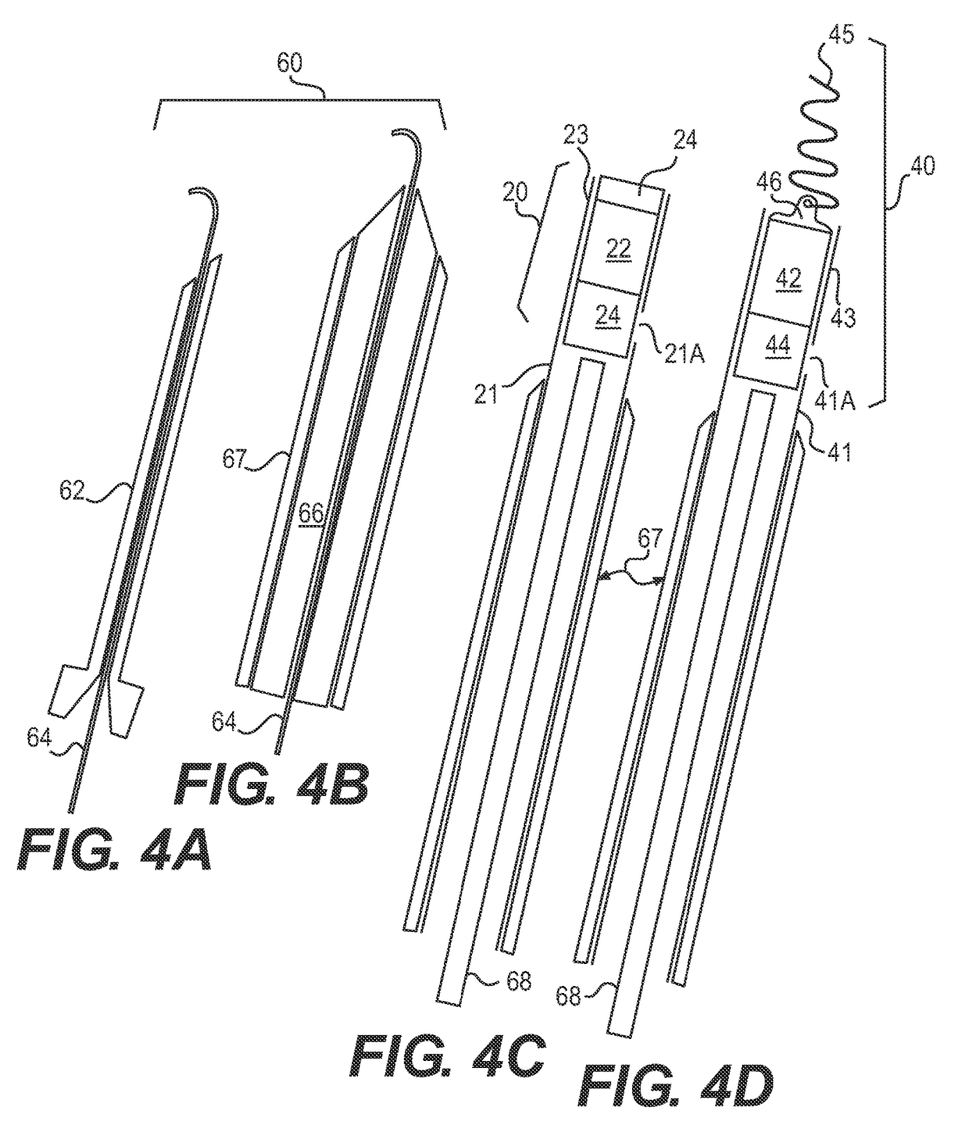
FIGS. 4A-4D illustrate various exemplary mechanical configurations of the implantation means as described in the narrative.

Turning now to the Figures, and specifically now referring to FIGS. 1, 2, and 4, the epicardial pacing system of the present invention comprises one or more implanted modules 20, 40, implantation means 60 for percutaneous implantation and fixation of the implanted modules, plus extracorporeal equipment 80 for programming, monitoring, and recharging the implanted modules under medical supervision via a recharging loop 82. The implanted modules are generally divided into two types: atrial modules 20 implanted via atrial insertion sheath 21, which perform signal detection and communication functions; and ventricular modules 40 implanted via ventricular insertion sheath 41, which perform signal detection, communication, and pacing functions via a penetrating myocardial electrode 45.

The invention encompasses various ways of using and combining these modules to treat specific types of cardiac arrhythmias, but it will be apparent to clinicians and others skilled in the art to combine these modules and their functionalities into other configurations not described explicitly herein. All such combinations fall within the scope of this invention.

More specifically, FIG. 2 illustrates the components and construction of the electronic subsystems according to embodiments of the invention. Extracorporeal equipment 80 includes a programming device 86 connected to a radio frequency (RF) generator/receiver 84 that can transmit power and data via recharging loop 82 through the patient's body and across the skin by inductive coupling to one or more implanted atrial modules 20 and/or one or more implanted ventricular modules 40. Extracorporeal equipment 80 can also include a local monitor 90 that is provided to a patient and/or his or her health care provider in order to interrogate the status of and stored data within his or her implanted modules via the bidirectional RF telemetry link. The local monitor 90 can provide various alerting functions to the patient and to the physician via various alarms, displays, user interfaces, telephone modems, internet connections, and other such means as are well-known in the art. The physical construction and electronic functions of the implanted modules are similar except for myocardial electrode 45 and hinged lead 46 of ventricular module 40. The implanted modules generally consist of or comprise hermetic or water-proof case 22 or 42 for protection of the electronics from body fluids, barb 23 or 43 for temporary fixation of the module within its insertion sheath 21 or 41, monolithic electrodes 24 or 44, at least one of which advantageously consists of or comprises the metal case of power cell 28 or 48, RF communication subsystem 29 or 49 capable of exchanging power and data with extracorporeal equipment 80, sensing means 32 or 52 connected to electrodes, pulsing means 34 or 54 connected to electrodes, digital signal processing (DSP) means 36 or 56 capable of executing programs and accessing and storing data in memory means 38 or 58 and power regulation means 39 or 59 capable of managing the flow of voltage and current to and from power cell 28 or 48.

In one preferred embodiment, the epicardial pacing system includes one atrial module 20 and one ventricular module 40 that communicate with each other by passing electrical pulses through the intervening tissues and that contain different programs for sensing and emitting electrical signals, as described below. In the illustrated preferred embodiment, the ventricular module 40 includes a myocardial electrode 45 that permits the electrical pulses that it produces to pace the heart whereas the atrial module 20 does not include such a myocardial electrode, but as will be apparent below, it is alternatively possible for the atrial module 20 to also include a myocardial electrode 45 that permits the electrical pulses that it produces to pace the heart as well. It is also possible to include in the epicardial pacing system additional ventricular modules 40 that can be synchronized so as to permit simultaneous or near simultaneous pacing of separate ventricular sites, which is useful in cases of cardiac dyschrony.

Figure 3:
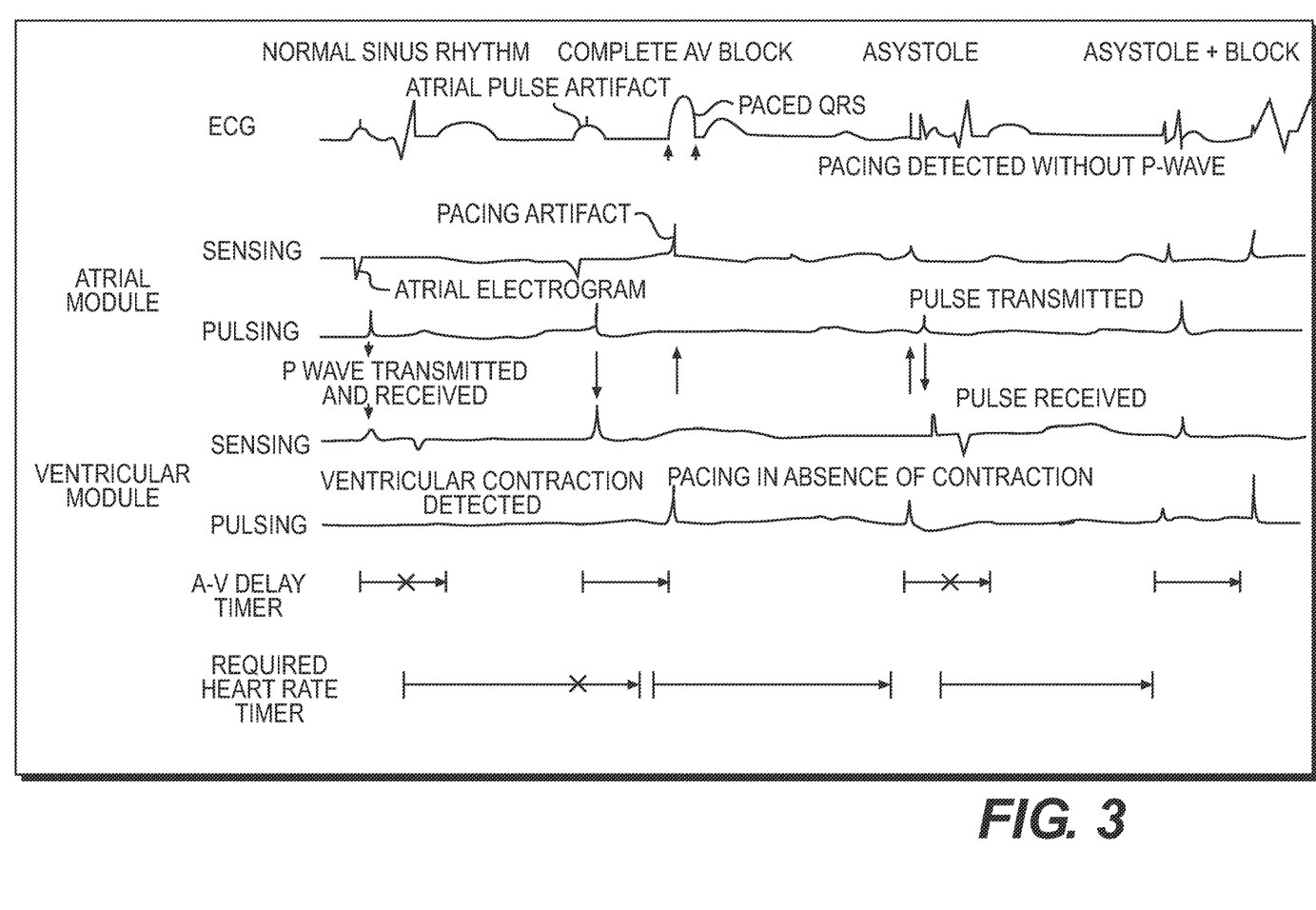
FIG. 3 provides a timing diagram of the sensing and pulsing functions of the implanted modules in relationship to the types of cardiac rhythm as they would be visualized in a conventional electrocardiogram (ECG) according to certain embodiments of the invention.

Referring to FIGS. 2 and 3, sensing means 32 in the atrial module 20 detects the presence of a P-wave in the adjacent atrium via monolithic electrodes 24 (or via its myocardial electrode 45 if so equipped) and then signal that detected event by emitting a brief current pulse generated by pulsing means 34 and conveyed into the surrounding tissue via monolithic electrodes 24 (or via its myocardial electrode 45 if so equipped). If atrial pacing is not desired, these brief current pulses will have a low enough energy to avoid capturing the atrial muscle (and causing a separate atrial contraction). If atrial pacing is desired and possible via a myocardial electrode 45, then these brief current pulses will have a higher energy. Note that these pulses are timed to occur immediately after the atrial sensed event. As a result the atria will have just depolarized in the normal manner and this atrial pacing pulse will occur during the obligatory atrial refractory period and will not result in electrical stimulation, which could otherwise result in atrial arrhythmias. Although these brief current pulses already have a low enough energy to avoid capturing the atrial muscle (and causing a separate atrial contraction), these pulses also are timed to occur immediately after the atrial sensed event, so that they occur during the obligatory atrial refractory period and do not result in electrical stimulation (or potential for atrial arrhythmias). Programmable electronics 30 for performing this and other functions described below also include hardware and/or software for digital signal processing (DSP) 36, hardware and/or software for memory 38, and various other switching and power monitoring and regulation functions as are well-known to those skilled in the art. Hardware and/or software for sensing 52 in the ventricular module 40 detect the electrical artifact that results from propagation of the brief current pulse emitted by atrial module 20 through the volume conductive tissues of the body. DSP 56 in the programmable electronics 50 of the ventricular module 40 evaluate fluctuations in the amplitude of successive transmissions from atrial module 20 in order to infer the respiratory rate of the patient. Changes in the volume of air in the lungs affect the impedance of the tissue between the two modules and, hence, the amplitude of the received electrical artifact, providing a simple way to determine the respiratory rate and to infer the metabolic demand of the patient, as is well-known in the art and described in more detail below. If desired for a given patient, the inferred respiratory rate is used by ventricular module 40 to establish a Required Heart rate that must be maintained by cardiac pacing if the ventricular rate drops below the Required Heart rate.

The receipt of an electrical artifact from atrial module 20 also provides the timing of a naturally occurring atrial contraction associated with the P-wave or of a paced atrial contraction caused by the brief current pulse emitted by atrial module 20. Referring to FIG. 3 and particularly to the first condition labeled "normal sinus rhythm", the receipt of the electrical artifact starts an A-V Delay timer in ventricular module 40 (of, for example, FIG. 2) while the hardware and/or software for sensing 52 look for the electrical signal that indicates that a ventricular contraction has occurred. The occurrence of the electrical signal before the programmed time limit (denoted by the X across the timeline of A-V Delay timer in FIG. 3) indicates that the ventricle has responded due to conduction of the atrial signal and that no ventricular pacing is required. The occurrence of the ventricular contraction starts another Required Heart rate timer in ventricular module 40, which looks for the next occurrence of an electrical artifact from atrial module 20 signifying the timing of a naturally occurring atrial contraction associated with the P-wave or of a paced atrial contraction caused by the brief current pulse emitted by atrial module 20. The occurrence of the electrical artifact before the programmed time limit (denoted by the X across the timeline of Required Heart rate timer in the second condition labeled "complete AV block") indicates that the atrium has initiated the next cardiac cycle at an adequate heart rate, so no pacing is yet required. A-V Delay timer in ventricular module 40 is restarted while the hardware and/or software for sensing 52 look for the electrical signal that indicates that a ventricular contraction has occurred. In the condition labeled "complete A-V block" in FIG. 3, no such electrical signal is received before the end of the A-V Delay time period, so the ventricle is paced by emitting a brief current pulse sufficient to cause ventricular contraction by ventricular module 40 via myocardial electrode 45. The Required Heart rate timer is then restarted while the ventricular module 40 waits to receive an electrical artifact from atrial module 20 signifying the timing of a naturally occurring atrial contraction associated with the P-wave or of a paced atrial contraction caused by the brief current pulse emitted by atrial module 20. The absence of an electrical artifact before the programmed time limit (as illustrated in the condition labeled "asystole" in FIG. 3) causes ventricular module 40 to start A-V Delay timer and to emit a weak current pulse which is insufficient to pace the ventricle but which generates an electrical artifact that is detected by atrial module 20. When detection occurs, atrial module 20 immediately generates a brief current pulse identical to those that it would generate in response to detecting a normal atrial electrogram corresponding to a P-wave. If the brief current pulse effectively paces the atrium and if there is normal conduction into the ventricles, ventricular module 40 will detect a ventricular contraction before the programmed time limit of the A-V Delay timer (denoted by the X across the timeline of A-V Delay timer in FIG. 3). In this case, no pacing is required and ventricular module 40 restarts its Required Heart rate timer. If the atrium has not been paced or there is conduction block as indicated in the condition labeled "asystole+block" in FIG. 3, then A-V Delay timer in ventricular module 40 will complete its count without detecting a ventricular contraction. Ventricular module 40 then generates a strong current pulse sufficient to pace the ventricle. It is important that the hardware and/or software for sensing in atrial module 20 be able to differentiate the artifact resulting from the strong current pulse from ventricular module 40, which elicits no response from atrial module 20 from the artifact resulting from the weak current pulse from ventricular module 40 and from the atrial electrogram, either of which trigger atrial module 20 to generate its own brief current pulse. Additionally, it is important that the hardware and/or software for sensing in ventricular module 40 be able to differentiate the artifact resulting from the current pulse from atrial module 20 from the non-artifact electrograms resulting from intrinsic ventricular activity in order to avoid interpreting other ventricular events (such as premature ventricular contractions) from artifact electrograms signifying atrial events.

It will be apparent to those normally skilled in the art of cardiac electrophysiology that epicardial pacing systems consistent with this invention can be configured with other numbers of individual modules. For example, some patients will require only a single ventricular module 40 that generates a strong current pulse sufficient to pace the ventricle whenever no ventricular contraction is detected within a preprogrammed Required Heart rate time limit. Other patients will require more than one ventricular module 40 to treat dyschrony between the ventricles. In this case, one ventricular module 40 could be programmed to have a Required Heart rate time limit that is always less than the other ventricular module(s) 40 so that it will act as the dominant pacemaker. When this dominant pacemaker generates a strong current pulse, the other, non-dominant ventricular module(s) 40 will detect the resulting electrical artifact in the same manner as they would detect the artifact resulting from a brief current pulse from an atrial module 20. The non-dominant ventricular module(s) 40 would then start their respective A-V Delay timers and each would generate a strong current pulse sufficient to pace the ventricle in which it is located if and only if no ventricular contraction were detected. Alternatively, two identical ventricular devices could be used whereby both respond equally (or with slight variability in AV Delay timers to allow for one ventricular site to pace just ahead of the other). In instances where one device may permit a shorter Required Heart rate time limit than the other (due to small changes in perceived respiratory rate), the slower device will detect the faster device's ventricular electrical artifact and time its AV Delay timer from the artifact.

In the above explanations, when sensing or pulsing means reference a single electrode, it should be assumed that one of the monolithic electrodes 24 or 44 on the corresponding module is used as a reference electrode to provide a complete electrical circuit with the body. As described in more detail below, each module will have at least one such monolithic electrode that acts as the ground or reference for its electronic circuitry, which may advantageously comprise or consist of or be electrically connected to the metal case of its power cell 28 or 48, respectively in the atrial 20 or ventricular 40 module.

The following is an example of one algorithmic method to determine the respiratory rate from the amplitude of the electrical artifact created by atrial module 20 and sensed by ventricular module 40. The range of amplitudes of the electrical artifacts sensed over time depends on many factors, including the distance between the two modules, their relative orientations, and the density of the intervening tissues. During inspiration, the lungs fill with air, reducing their density and electrical conductance and reducing the amplitude of the electrical artifacts. By averaging all of the amplitudes measured over a period of time encompassing many respiratory cycles, it is possible to determine an accurate mean amplitude. The mean amplitude can be used as a threshold for comparison with each individual measurement in order to determine whether the lungs are inflating or deflating. When the sign of the difference between the amplitude of the artifact and this threshold transitions from positive to negative, this indicates the mid-point of inspiration. When the sign of said difference transitions from negative to positive, this indicates the mid-point of expiration. The heart rate is generally more than twice as fast as the respiratory rate, assuring that there will always be sufficiently frequent measurements to avoid an error condition known as aliasing in which respiratory cycles might be missed.

The implantation means 60 and its deployment for percutaneous implantation of atrial module 20 and ventricular module 40 in the pericardial space surrounding the heart are described with reference to FIG. 4. Hypodermic needle 62 is used to introduce guide wire 64 into the pericardial space behind the heart under fluoroscopic guidance from a subxyphoid approach, using the configuration in FIG. 4A. This technique is commonly used for pericardial ablations and is well-known to cardiologists who perform that procedure. After the tip of guide wire 64 is within the pericardial space, hypodermic needle 62 is withdrawn over the wire and replaced by dilator 66 and sleeve 67 which are advanced through the skin and intervening tissues until their distal ends are also in the pericardial space, using the configuration in FIG. 4B. Dilator 66 and guide wire 64 are removed from sleeve 67 and replaced by atrial insertion sheath 21 with atrial module 20 affixed within its distal portion. Atrial sheath 21 is advanced under fluoroscopic guidance through the lumen of sleeve 67 until atrial module 20 is located adjacent to the right or left atrium, as desired by the cardiologist for reliable detection of the P-wave associated with atrial contraction. Atrial insertion sheath 21 is advantageously a thin-wall, semiflexible tube made from a somewhat elastic polymer as known in the art, enabling it to deform around the beating heart. Atrial module 20 advantageously has barbs 23 or other features whose outside diameter pushes against a portion of the inside surface of atrial insertion sheath 21, thus tending to keep atrial module 20 affixed from frictional forces, as described by Kaplan and Loeb (2009) and in PCT/US2013/035377 and incorporated by reference in their entireties. Atrial insertion sheath 21 advantageously contains a fenestration 21A as illustrated, allowing both of its monolithic electrodes 24 to make electrical contact with the surrounding tissues and liquids.

The fenestration plus sensing means 32 and other functions of the programmable electronics 30 described above enables reliable detection of P-waves to be ascertained electrophysiologically during insertion and before release of atrial module 20 from insertion sheath 21. When atrial module 20 is correctly located, it is expelled from insertion sheath 21 by inserting pusher 68 into insertion sheath 21 until its tip is located behind atrial module 20 and subsequently withdrawing insertion sheath 21 over pusher 68, thus overcoming the frictional forces.

Figures 5A, 5B:
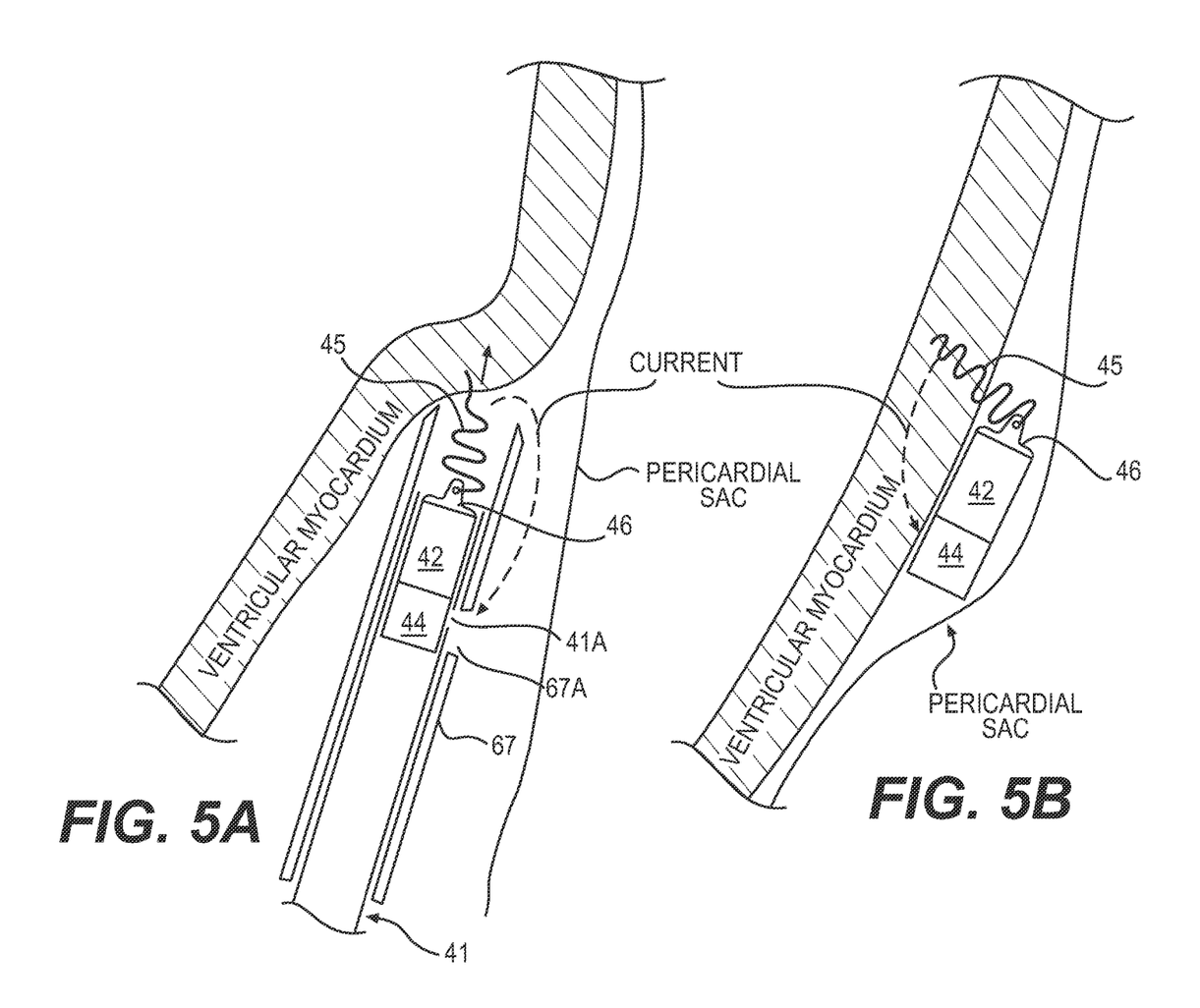
FIGS. 5A and 5B illustrate the steps in implantation and fixation of a ventricular implantable module to the ventricular myocardium within the pericardial sac.

The configuration for percutaneous implantation of ventricular module 40 in the pericardial space surrounding the heart is described with reference to FIG. 4D. This assumes that the tip of sleeve 67 is already located in the epicardial space as described above for implantation of the atrial module 20. As illustrated in FIG. 5A, ventricular insertion sheath 41 with ventricular module 40 affixed within its distal portion is advanced under fluoroscopic guidance through the lumen of sleeve 67 until ventricular module 40 is located adjacent to the right or left ventricle, as desired by the cardiologist for pacing. Ventricular insertion sheath 41 is advantageously a tube that is somewhat more rigid than the atrial insertion sheath 21, which can be achieved by making it with a thicker wall or from a material with a higher Young's modulus, such as Vectra, a liquid crystal polymer that can be filled with reinforcing glass fibers and extruded to have particularly high bending stiffness, as described by Kaplan and Loeb (2009, Annals of Biomedical Engineering, Vol. 37, pp. 1858-1870) and incorporated herein by reference. Ventricular module 40 advantageously has barbs 43 or other features whose outside diameter pushes against a portion of the inside surface of ventricular insertion sheath 41, thus tending to keep ventricular module 40 affixed from frictional forces, as described by Kaplan and Loeb (2009) and in PCT/US2013/035377, which is incorporated by reference in its entirety. Ventricular insertion sheath 41 and sleeve 67 advantageously contain fenestrations 41A and 67A, respectively, as illustrated, allowing monolithic electrode 24 to make electrical contact with the surrounding tissues and liquids. Ventricular module 40 includes a myocardial electrode 45 made from a relatively stiff material that is formed into the shape of a corkscrew with a sharpened tip. Myocardial electrode 45 is connected mechanically and electrically to the distal end of ventricular module 40 by hinged lead 46 (also referred to herein simply as "hinge"). Both myocardial electrode 45 and hinged lead 46 are insulated by a thin layer (not illustrated) of a dielectric material, such as Parylene, except for the distal most portion of myocardial electrode 45. Myocardial electrode 45 is advantageously made from pure iridium, which has a high Young's modulus and hardness for forming the sharpened corkscrew and which can be electrochemically activated at its exposed tip to provide a low impedance and energy efficient interface for conveying pacing pulses into the myocardium, as is well-known in the art of cardiac pacing electrodes. However, it can be made of any suitable material. Hinge 46 is advantageously made from pure iridium or an alloy of platinum and iridium that has a high Young's modulus and good electrical conductivity on its surface where it mates with the proximal end of myocardial electrode. However, it can be made of any suitable material. The positioning of ventricular module 40 within ventricular insertion sheath 41 is such that myocardial electrode 45 protrudes from the distal end of ventricular insertion sheath 41, allowing it to be pushed against the epicardial surface of the ventricular myocardium. The convex curvature of the ventricular myocardium, the narrow confines of the pericardial sack and the stiffness of ventricular insertion sheath 41 together cause the myocardial electrode 45 to lie against the distorted myocardial surface as illustrated in FIG. 5A. It might be advantageous to visualize the surface of the myocardium at the end of sleeve 67 to look for coronary blood vessels before approaching it with the sharp tip of myocardial electrode 45. This can be accomplished by inserting a fiber-optic bundle, miniature video camera, or ultrasound probe on the end of a catheter into sleeve 67 before inserting ventricular insertion sheath 41 bearing ventricular module 40.

Note that hinge 46 has asymmetrical shoulders such that in the orientation illustrated in FIG. 5A, the basal-most corkscrew turn of myocardial electrode 45 rests against the rightmost shoulder which acts as a stop preventing clockwise pivoting beyond the position illustrated. This permits the operator to transmit leftward translational forces against the ventricular myocardium through relatively stiff ventricular insertion sheath 41 and myocardial electrode 45. Axial rotation applied manually to the external portion of ventricular insertion sheath 41 causes myocardial electrode 45 to penetrate and become affixed to the myocardial wall. This desirable condition can be ascertained electrophysiologically by observing the pacing effects of electrical current pulses (dashed lines in FIG. 5) applied to the ventricle by pulsing means 54 via myocardial electrode 45 and monolithic electrode 44 through the fenestrations. When ventricular module 40 is correctly affixed, it is expelled from insertion sheath 41 by inserting pusher 68 into insertion sheath 41 until its tip is located behind ventricular module 40 and subsequently withdrawing insertion sheath 41 and sleeve 67 over pusher 68, thus overcoming the frictional forces. As the distorted myocardial surface returns to its normal configuration against the pericardial sack, myocardial electrode 45 rotates on hinge 46 as illustrated in FIG. 5B. Note that ventricular module 40 was released in the same axial orientation as in FIG. 5A, in which the orientation of myocardial electrode 45 is free to rotate in the clockwise direction to a full 90° angle. During subsequent ventricular contractions, motion at hinge 46 can relieve stress on the myocardial tissue arising from the relatively rigid myocardial electrode 45 and case 42. The correct axial orientation of hinge 46 can be ascertained by the incorporation of fiducial marks on the proximal, visible surface of ventricular insertion sheath 41 showing the orientation of the ventricular module 40 within its distal end.

Figures 6A, 6B, 6C, 6D:
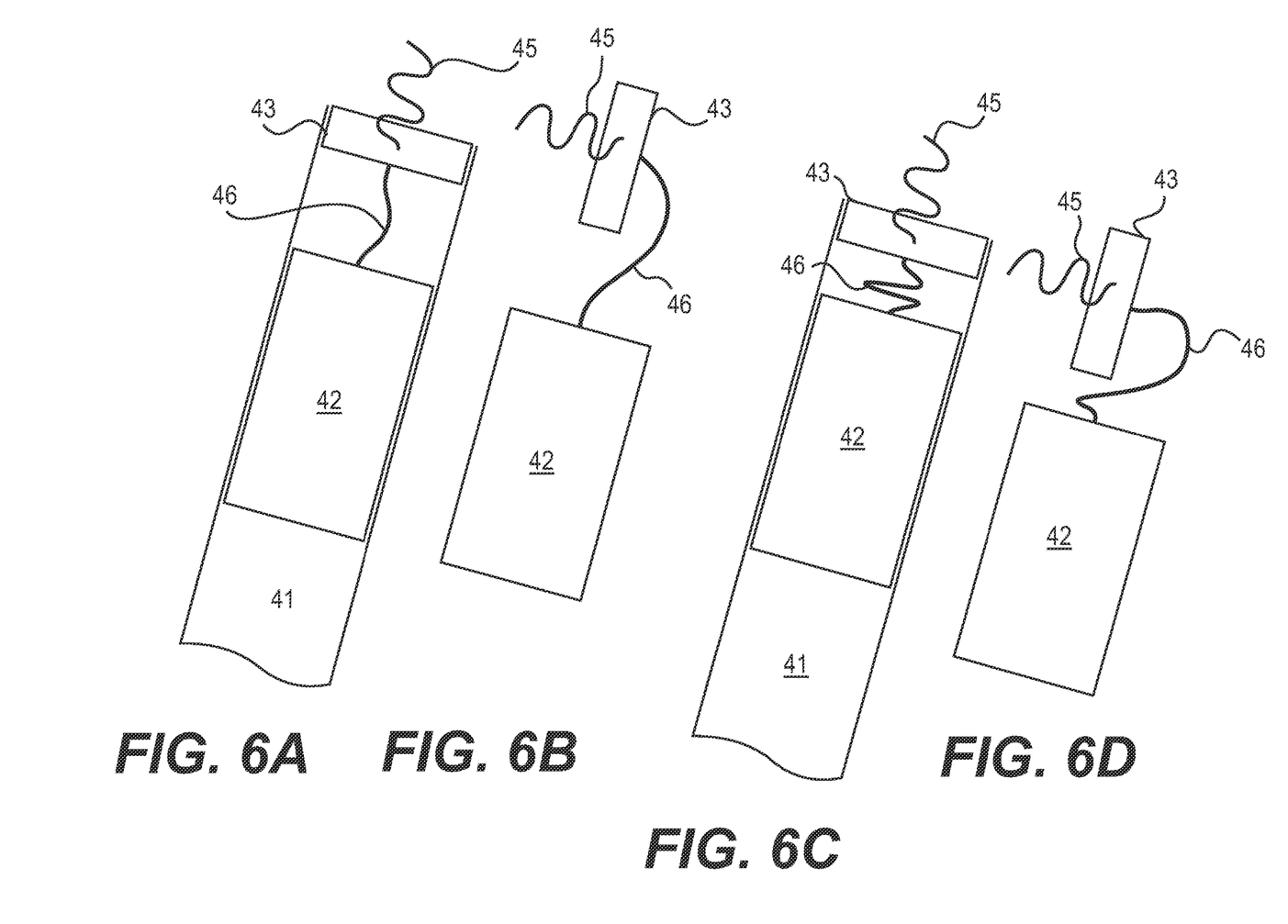

It is to be understood that the concept of a hinged connection is not limited to the embodiments of the invention described above, but instead can be applied to any type of pacemaker or pacemaker system in which the pacemaker is fully deployed within the pericardial sac, such as, for example, the systems described in U.S. patent application publication number 2012/0078267 and U.S. provisional patent application No. 61/620,701, filed 5 Apr. 2012, the entire disclosures of which are incorporated herein by reference. Likewise, the concept of a "hinged lead" or simply a "hinge" should be understood by the skilled artisan to include all structures encompassed by the general definition of "hinge" known in the art (see, for example, www dot dictionary doc com (access date 3 May 2014), which defines a hinge as "a jointed device or flexible piece on which a door, gate, shutter, lid, or other attached part turns, swings, or moves"). A hinge according to the present invention thus includes, but is not limited to a flexible, durable structure that can withstand numerous (e.g., millions or more) flexations without significant loss of intended function. As used herein, "flexations" relates to the amount of flexing required for a hinge to accommodate the natural beating of a heart, and excludes flexations that are insufficient to provide that function. Furthermore, the concept of allowing for the pacemaker to lie parallel or substantially parallel to the myocardium and pericardial sac is not limited to the design depicted in FIG. 5. For example, an alternative design, such as that depicted in FIG. 6 and FIG. 7, uses a material that can be temporarily deformed when subjected to pressure, but returns to its original shape once the pressure is released to perform the function of hinge 46. As illustrated in FIGS. 6A and 6C, base 43 for retaining the assembly in sheath 41 and aligning myocardial electrode 45 axially during insertion into the myocardium is located at the electrical and mechanical joint between myocardial electrode 45 and case 42. The flexible material comprising hinge 46 may be fabricated so as to have one of various possible resting configurations that it assumes after release of the pacemaker from sheath 41, as illustrated in FIGS. 6B and 6D. In the example in FIGS. 6A and B, a single coil (illustrated as a single loop, but other embodiments contain multiple loops) with a natural 90 degree curve can be used as a connection between myocardial electrode 45 in the form of a corkscrew and a pacemaker case 42. Although the coil has a 90 degree bend in its "natural" form, it can be "straightened" so that pacemaker case 42 and electrode 45 are coaxial during the insertion process (when the system is housed in a sheath) and implantation can occur via directly screwing into the epicardium. When the device is released from the sheath, the natural 90 degree curve will return, allowing case 42 to rest parallel or substantially parallel to the epicardial surface (thereby reducing the forces for lead dislodgement). The term "substantially parallel" is intended to address the fact that the epicardium of the heart is not a flat surface and is constantly changing shape while beating. FIGS. 6C and 6D depict a more complex form for the flexible material used in hinge 46 in which it has a coiled or otherwise convoluted form, which may advantageously assist in transferring axial force to base 43 so as to eject it from sheath 41 during deployment.

Figure 7:
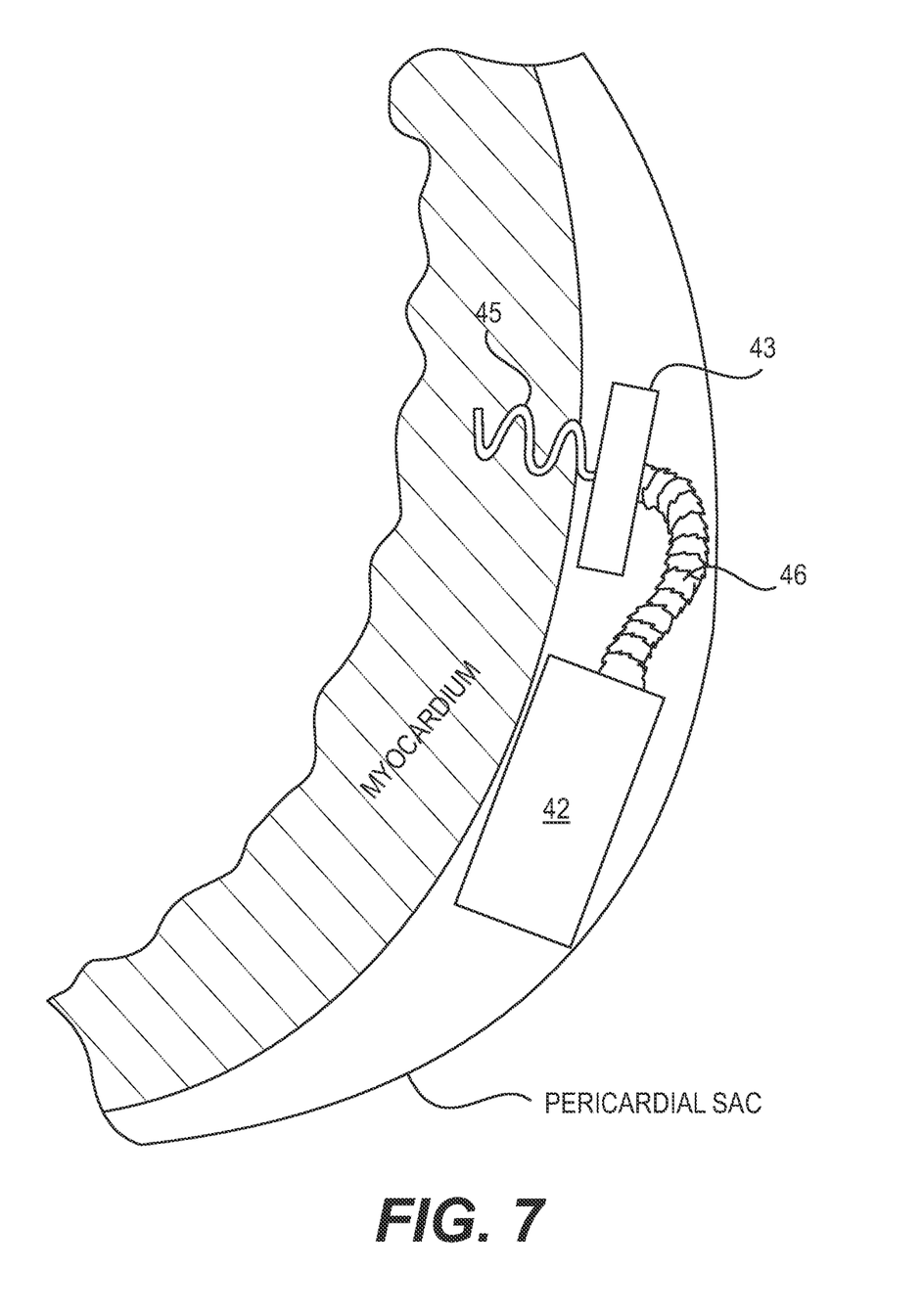
FIG. 7 illustrates the relationship of the deployed pacemaker body and electrode to the anatomical structures of the myocardium and pericardial sac.

FIG. 7 shows the resting configuration of a deployed epicardial pacemaker in which electrode 45 is located within the myocardium, base 43 lies substantially flat on the epicardial surface, and hinge 46 provides the electrical connection between electrode 45 and pacemaker circuitry in case 42 between the myocardium and the pericardial sac while elastically absorbing the motion of the beating heart. As illustrated in FIG. 7, hinge 46 is advantageously made from a superelastic material such as the metal alloy nitinol that has been formed into a cylinder with many openings in its wall such as the design of an intravascular stent. In this application, such an open-lattice structure provides a highly compliant and elastic electrical lead that will withstand millions of cycles of bending and will not transmit substantial forces to myocardial electrode 45 that might cause it to be dislodged. While not limiting the size of the module in any way, for example, hinged leads 20 and/or 40 can be advantageously fabricated in a generally tubular shape having a diameter of 0.75 mm and a length of 20 mm. Of course, the dimensions can easily be changed depending on the size of the subject into which it will be implanted and other surgical considerations using standard procedures known in the art.

Figure 8:
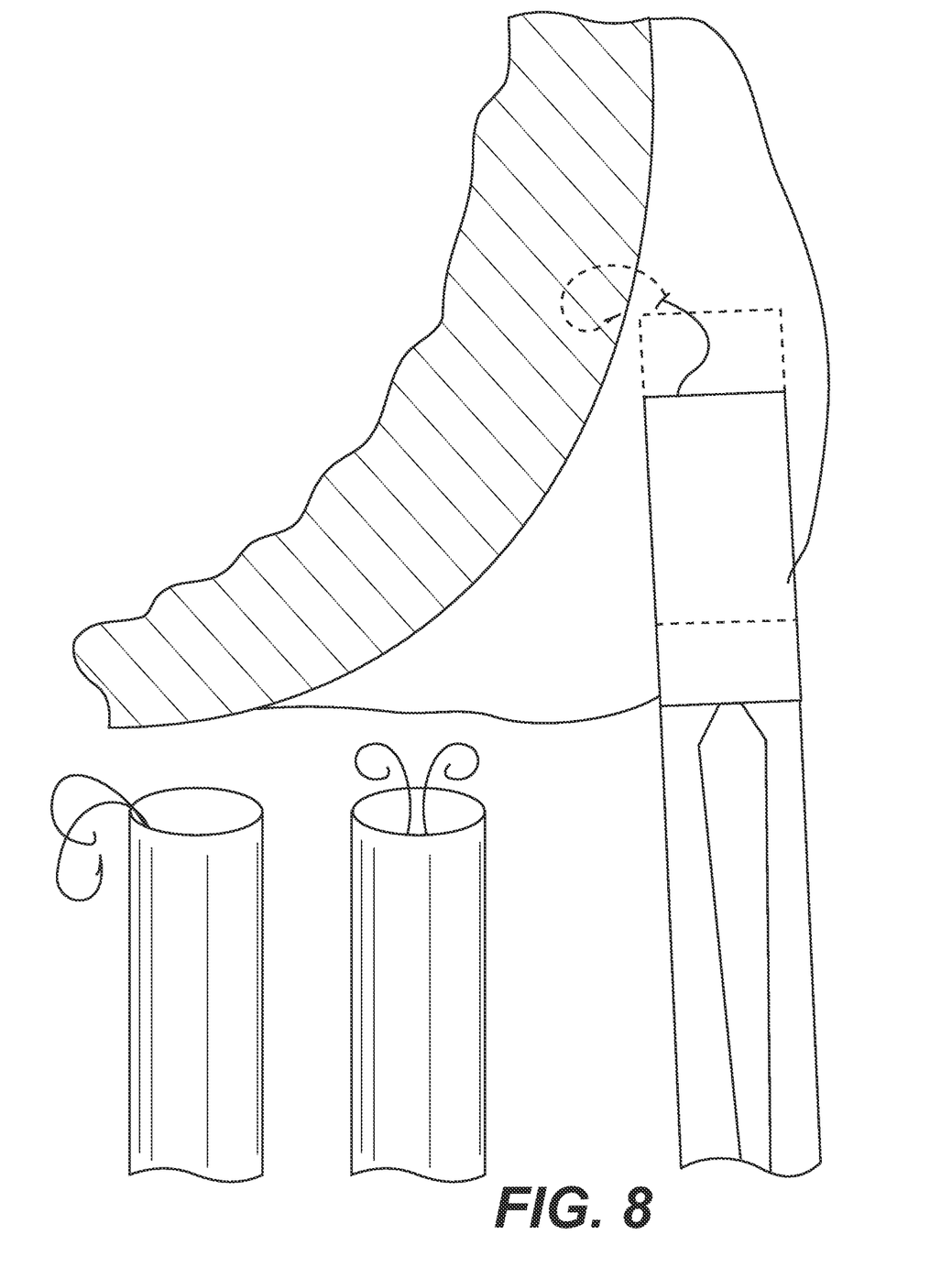
FIG. 8 illustrates another embodiment of the invention in which a lead having a natural bend has a fishhook-style tip, allowing the pacemaker, once deployed, to lie parallel to the myocardium and epicardial sac.

As an additional example of alternative designs that allow a pacemaker to lie flat against the epicardial surface, FIG. 8 depicts a fishhook design for the lead, which allows for a 90 degree turn between the pacemaker electrode and the pacemaker body.

In all of the configurations illustrated herein, it is to be understood that the electrode/hinge and electrical connection to the pacemaker circuitry should be insulated from electrical contact with the body fluids along all surfaces except for the distal end of the electrode that is intended to deliver electrical current into the body. This is advantageously provided by a thin layer of a vapor deposited polymer, such as various paraxylylenes known under the tradename of Parylene, which can completely cover even mechanically complex structures such as the various hinges, coiled springs, and stent structures illustrated herein, as described in co-pending PCT patent application number PCT/US2012/020701, filed 10 Jan. 2012, the entire disclosure of which is hereby incorporated herein by reference.

Various alternative configurations of implanted modules are possible to treat various cardiac conditions, taking advantage of the flexibility afforded by the programmable electronics 30 and 50 associated with atrial modules 20 and ventricular modules 40, respectively. In one preferred embodiment, it is possible to implant only one ventricular module 40 with no atrial module 20, and to program the ventricular module 40 to operate autonomously as a fixed rate pacemaker, either continuously or in a demand mode when ventricular contractions are not sensed at greater than the fixed rate. In another preferred embodiment, it is possible to implant two or more ventricular modules 40 with or without an atrial module 20 and to cause pacing output by one ventricular module 40 to be sensed by and used to synchronize pacing output of the other ventricular module(s) 40. In another preferred embodiment, it is possible to implant an atrial module with similar electrode and hinge as the ventricular device (with or without ventricular module 40) to allow for both atrial pacing with or without ventricular pacing. In yet another preferred embodiment, any of the implanted modules could include an accelerometer to detect rapid movement of the patient indicative of exercise in order to make the minimal pacing rate responsive to metabolic demand. In this case, it may be advantageous to use a multiaxis accelerometer in order to separate the motion induced by the contractions of the adjacent heart from the motion associated with physical exercise. The algorithmic functions and sensing and stimulation parameters required by these and other configurations are transmitted by programming device 86 to the implanted modules via a bidirectional radio frequency (RF) telemetry link consisting of RF generator/receiver 84 and recharging loop 82 in the extracorporeal equipment 80 and RF communications subsystems 29 and 49 within atrial modules 20 and ventricular modules 40, respectively. The algorithms and parameters are stored within programmable electronics 30 and 50, which include memory means 38 and 58 and DSP means 36 and 56, respectively for atrial modules 20 and ventricular modules 40. The bidirectional RF telemetry link is used to transmit power from extracorporeal equipment 80 to various implanted modules as needed to recharge their power cells 28 and 48. Because the relative orientation and distance between recharging loop 82 and the one or more implanted modules can vary, it is necessary that each implanted module contain a power regulator 39 or 59 in order to monitor the state of charge of its power cell 28 or 48 and to control and regulate the recharging current applied thereto. Because of the mismatch in size between the recharging loop 82 and the tiny inductive coil that is part of the RF communication system 29 or 49 of each epicardial implant, it is necessary to generate a relatively high RF magnetic field in recharging loop 82, such as by use of a class E oscillator operating within the 6.78 MHz ISM band and driving a recharging loop 82 with a high-Q via an impedance matching network. Data specifying algorithmic functions and sensing and stimulation parameters are encoded for transmission inward by modulation of the RF carrier produced by RF generator/receiver 84. Data specifying the status of implanted modules 20 and 40, records of sensed and paced events, and the condition of their power cells 28 and 48 are encoded for transmission outward by modulating the load presented by their corresponding RF communication subsystems 29 and 49, thereby generating a reflected subcarrier, as described in Troyk, P. R., I. E. Brown, W. H. Moore and G. E. Loeb (2001, "Development of BION Technology for Functional Electrical Stimulation: Bidirectional Telemetry", Istanbul, Turkey, Proc. 23rd Annual International Conference of the IEEE Engineering in Medicine and Biology Society) and incorporated herein by reference. Each implanted module has a unique identification code which its DSP uses to decide which inward data transmissions are intended for it. Various means for transmitting power, encoding data and modulating carriers are well-known in the art and fall within the scope of this invention.

It will be apparent to those skilled in the art that various modifications and variations can be made in the practice of the present invention and in construction of the device without departing from the scope or spirit of the invention. Other embodiments of the invention will be apparent to those skilled in the art from consideration of the specification and practice of the invention. It is intended that the specification and examples be considered as exemplary only.

The invention claimed is:

1. A minimally-invasive, modular epicardial pacemaker system, said system comprising:
    a first pacemaker unit adapted to be implanted between atrial epicardial tissue of an atrium of a heart and a pericardial sac surrounding the heart, and electrically connected to atrial myocardial tissue of the heart;
    a second pacemaker unit adapted to be embedded in ventricular tissue of a ventricle of the heart; and
    wherein at least one of the first pacemaker unit and the second pacemaker unit has the following features:
        an electrode for delivering an electrical pulse to myocardial tissue of the heart in need thereof;
        the pacemaker suitable for delivering electrical pacing to the heart in need thereof; and
        a hinge having asymmetric shoulders and physically connecting the electrode to the pacemaker, wherein the hinge allows the electrode and pacemaker to be angularly aligned substantially along a same path prior to deployment into cardiac tissue, but then allows the two to pivot with respect to each other such that the pacemaker can lie substantially parallel to epicardium, and between the epicardium and the pericardial sac, while the electrode remains substantially perpendicular to the epicardium;
    wherein the first and the second pacemakers communicate with each other to convey information about cardiac rhythm, pacing events, or both so as to coordinately pace the atrium and the ventricle of the heart, wherein the information comprises data indicative of respiration rate of a patient.

2. The system of claim 1, wherein the information comprises data that match predetermined demand and pacing data for the first and second pacemakers.

3. The system of claim 2, wherein the data is derived from measurements of changes in electrical currents between the two pacemakers, wherein changes indicate differences in density and/or volume of a chest cavity of the patient in which the system is deployed.

4. A process of implanting an atrial pacemaker unit into a patient, said process comprising:
    using a hypodermic needle to introduce a guide wire into a pericardial space of a heart from a subxyphoid approach;
    withdrawing the hypodermic needle over the wire;
    replacing the hypodermic needle with a dilator and a sleeve, which are advanced through skin and intervening tissues until their distal ends are also in the pericardial space;
    removing the dilator and the guide wire from the sleeve;
    replacing the dilator and the guide wire with an atrial insertion sheath, which includes an atrial module affixed within its distal portion, the atrial module including a separable base having a pair of substantially immovable barbs fixedly attached to and projecting permanently from the base portion in a perpendicular direction with respect to the longitudinal axis of the atrial module, wherein tip to tip distance of the barbs form a permanent fixed diameter which is larger than the atrial module outer diameter and adapted to push against the inside surface of the atrial insertion sheath whose internal diameter is greater than the atrial module outer diameter; and
    advancing the atrial insertion sheath through a lumen of the sleeve until the atrial module is located adjacent to an atrium and within the pericardial space;
    wherein the atrial module participates in pacing of a heart by electrical stimulation of myocardial tissue by sensing atrial contraction events and communicating the occurrence of such events to a second cardiac pacemaker, which is electrically connected to ventricular myocardial tissue of the heart.

5. The process of claim 4, wherein the insertion sheath has a fenestration.

6. The process of claim 5, wherein the fenestration is adapted to allow the electrode to make electrical contact with myocardial tissue.

7. The process of claim 6, further comprising a sensor which detects P-waves during insertion and before release of the pacemaker module from the insertion sheath.

8. The process of claim 7, wherein the pacemaker module is adapted to be expelled from the insertion sheath when a sufficient force is applied to overcome friction caused by tips of immovable barbs on the atrial module against the inside surface of the insertion sheath.

9. A process of implanting a pacemaker unit into a patient, said process comprising:
    using a hypodermic needle to introduce a guide wire into a pericardial space of a heart from a subxyphoid approach;
    withdrawing the hypodermic needle over the guide wire;
    replacing the hypodermic needle with a dilator and a sleeve, which are advanced until their distal ends are also in the pericardial space;
    removing the dilator and guide wire from the sleeve;
    replacing the dilator and guide wire with a sheath, which includes a pacemaker unit affixed within its distal portion;
    advancing the sheath through a lumen of the sleeve until the pacemaker unit is located adjacent to an atrium or ventricle and within the pericardial space; and
    optionally implanting an electrode of the pacemaker unit into myocardium of the heart by way of epicardium, wherein the pacemaker unit comprises:

an electrode for delivering an electrical pulse to myocardial tissue of the heart in need thereof;

a cardiac pacemaker suitable for delivering electrical pacing to the heart in need thereof; and a hinge having asymmetric shoulders and physically connecting the electrode to the pacemaker, wherein the hinge allows the electrode and pacemaker to be angularly aligned substantially along a same path prior to deployment into cardiac tissue, but then allows the two to pivot with respect to each other such that the pacemaker can lie substantially parallel to the epicardium/myocardium/pericardial sac, and between the epicardium and pericardial sac, while the electrode remains substantially perpendicular to the epicardium/myocardium.

10. The process of claim 9, wherein the hinge comprises a lead that includes a bend that allows the pacemaker portion to lie substantially parallel to the epicardium/myocardium/pericardial sac, and between the epicardium and pericardial sac, while the electrode remains substantially perpendicular to the epicardium/myocardium.

11. The process of claim 10, wherein the bend in the lead is approximately 90°.

\* \* \* \* \*